United States Patent [19]

Gilbert

[11] 3,941,812

[45] Mar. 2, 1976

[54] THERMALLY STABLE OCTANITRO MACROCYCLIC EXPLOSIVES

[75] Inventor: Everett E. Gilbert, Morristown, N.J.

[73] Assignee: The United States of America as represented by the Secretary of the Army, Washington, D.C.

[22] Filed: Apr. 10, 1975

[21] Appl. No.: 566,848

[52] U.S. Cl. ............... 260/338; 149/105; 260/340.3
[51] Int. Cl.² ........................................ C07D 323/00
[58] Field of Search ......... 149/105; 260/338, 340.3, 260/645

[56] References Cited
OTHER PUBLICATIONS

Fuson et al., J. Am. Chem. Soc., Vol. 75, pp. 1325–1327, (1953).
Urbanski, Chemistry and Technology of Explosives, Vol. I, The MacMillan Co., New York, 1964, pp. 549–553.

*Primary Examiner*—Leland A. Sebastian
*Attorney, Agent, or Firm*—Nathan Edelberg; Robert P. Gibson; A. Victor Erkkila

[57] ABSTRACT

Novel compounds are provided having the formula

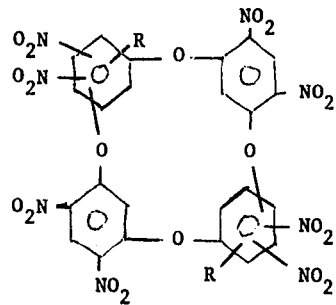

wherein R is hydrogen or lower n-alkyl and the ether oxygen atoms are attached in the 1,3 or 1,4 positions to the R substituted benzene rings, R being in the 2 or 5 positions when the ether oxygen atoms are in the 1,3 positions and R is lower n-alkyl.

These compounds are useful as explosives characterized by good thermal stability.

11 Claims, No Drawings

THERMALLY STABLE OCTANITRO MACROCYCLIC EXPLOSIVES

GOVERNMENTAL INTEREST

The invention described herein may be manufactured, used and licensed by or for the Government for governmental purposes without the payment to me of any royalty thereon.

BACKGROUND OF THE INVENTION

Supersonic aircraft, new types of missiles and equipment for space exploration require explosives, which exhibit better heat resistance than that characteristic of the known conventional explosives, e.g. TNT and RDX. A number of such explosives of superior thermal stability have been developed, but their widespread use has been hampered by the lack of availability due to their high cost.

SUMMARY AND DETAILED DESCRIPTION OF THE INVENTION

In accordance with this invention there is provided a class of novel octanitro macrocyclic explosive compounds, which possess better thermal stability than conventional explosives and can be made at relatively low cost. The novel compounds have the formula:

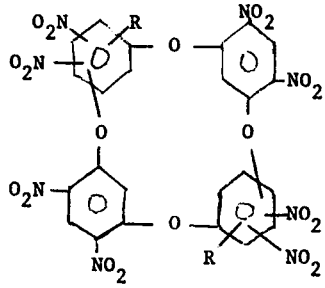

wherein R is hydrogen or lower n-alkyl and the ether oxygen atoms are attached in the 1,3 or 1,4 positions to the R substituted benzene rings, R being in the 2 or 5 positions when the ether oxygen atoms are in the 1,3 positions and R is lower n-alkyl. The term lower n-alkyl as used herein means an n-alkyl group of from 1 to 6 carbon atoms inclusive, i.e. methyl, ethyl, n-propyl, n-butyl, n-amyl and n-hexyl.

The novel compounds of the foregoing formula can be prepared by reacting with concentrated (e.g. 98–100%) nitric acid an intermediate nitro compound of the formula:

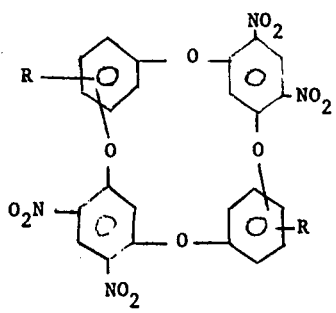

wherein R is hydrogen, lower n-alkyl or nitro and the ether oxygen atoms are attached in the 1,3 or 1,4 positions to the R substituted benzene rings, R being in the 2 or 5 positions when the ether oxygen atoms are in the 1,3 positions and R is lower n-alkyl or nitro. The nitration of the intermediate nitro compounds to produce the novel octanitro compounds is preferably accomplished by heating with a mixture of concentrated (e.g. 98–100%) nitric acid and concentrated (e.g. 95–100%) sulfuric acid, using a large excess (e.g. 10–20 times) over the amount theoretically required for the nitration reaction. By this method it was not found possible to produce a compound of said ring system containing more than eight nitro groups, since only destructive oxidation was noted, i.e. not more than two nitro groups per benzene ring could be introduced into the aforesaid intermediate compound, including the compound already containing a nitro group (R = nitro). The octanitro compound thus obtained can be precipitated by diluting the nitration reaction mixture with water, and purified by recrystallization from a suitable solvent, such as N,N-dimethylformamide, 2-pentanone and nitrobenzene.

The aforesaid intermediate nitro compounds can be readily prepared by reacting 1,3-dichloro-4,6-dinitrobenzene with a resorcinol or hydroquinone compound of the formulas

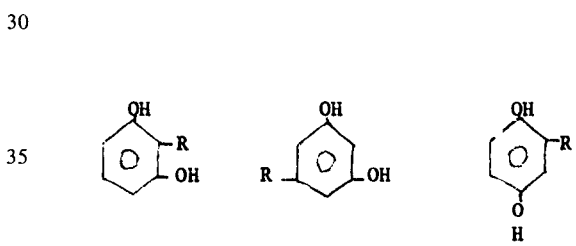

wherein R is hydrogen, lower n-alkyl or nitro, by methods known in the art. For example, the 1,3-dichloro-4,6-dinitrobenzene and the resorcinol or hydroquinone compound are heated together in approximately equimolecular proportions in the presence of an organic solvent, such as dimethylformamide, dimethylsulfoxide, and methyl-2-pyrrolidinone, and an acid binding agent, e.g. sodium carbonate and sodium bicarbonate. Advantageously, the reaction is carried out at an elevated temperature up to 150°C. or higher. The intermediate nitro compound thus produced can be separated by precipitation and filtration from the reaction mixture after cooling or dilution with water, washed with water to remove inorganic salts and purified by conventional methods, e.g. recrystallization from a solvent, such as nitrobenzene or extraction with a solvent in which it is insoluble but impurities are soluble, e.g. 1-propanol.

In place of 1,3-dichloro-4,6-dinitrobenzene, the 1,3-dibromo-, 1,3-difluoro- and 1,3-diiodo-4,6-dinitrobenzenes can be employed.

The intermediate nitro compounds thus obtained from resorcinol and hydroquinone have the following formulas:

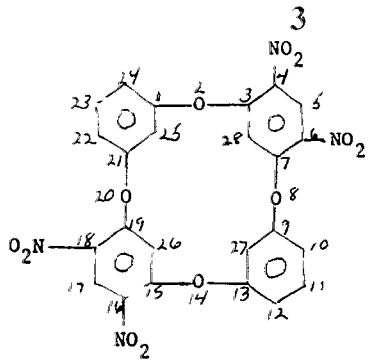
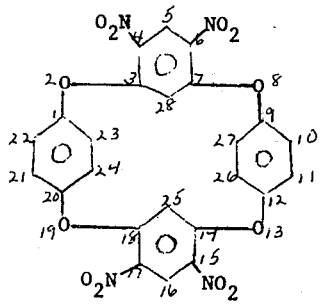

The Chemical Abstracts nomenclature for these compounds is as follows:

I  4,6,16,18-tetranitro-2,8,14,20-tetraoxapentacyclo[19.3.1.1$^{3,7}$1$^{9,13}$.1$^{15,19}$]octacosa-1(25),3,5,7(28),9,11,13(27),15,17,19(26),21,23-dodecaene II  4,6,15,17-tetranitro-2,8,13,19-tetraoxapentacyclo[18.2.2.2$^{9,12}$.1$^{3,7}$.1$^{14,18}$]-octacosa-3,5,7(28),9,11,14,16,18(25),20,22,23,26-dodecaene.

In view of the complexity of nomenclature, these compounds will be designated simply by the Roman numerals I and II, and derivatives thereof will be named by the substituents on the numbered ring systems of I and II.

The following examples provide further specific illustrations of the novel explosive compounds of the present invention.

EXAMPLE 1.

Part A

A mixture of 9.6g (0.04 mole) of 1,3-dichloro-4,6-dinitrobenzene, 4.4g (0.04 mole) or resorcinol, 6.8g (0.08 mole) of sodium bicarbonate and 150 ml. of N,N-dimethylformamide (DMF) was heated to 140°–145°C. and agitated at that temperature for 2 hours. The reaction mixture was then mixed with about 10 volumes of water, and the mixture was boiled for 1 hour and filtered. The filter cake was dried and extracted with hot acetonitrile to remove impurities, yielding 7.6g (69% of theory) of I, dec. 373°C. By recrystallizing from nitrobenzene or DMF, a product dec. 375°C. was obtained.

The structure of I was proven by elemental analysis for C, H and N, molecular weight determination using mass spectrometry, and proton nuclear magnetic resonance (NMR) — see Table I below:

Part B

Conversion of I to the octanitro compound.

A mixture of 5.5g (0.01 mole) of compound I, 11.5g of 98% nitric acid and 92g of 96% sulfuric acid was heated to 90°C. for 2 hours. The reaction mixture was cooled and poured into 500 ml. cold water, and the precipitate thus obtained was isolated by filtration, washed with water and dried. The yield of octanitro compound thus obtained was 7.0 grams, corresponding to 96% of theory. It flashed at 368°C. The structure of the octanitro compound (after recrystallization from 2-pentanone) was established by elemental analysis, molecular weight determination by mass spectrometry and NMR spectra as the 10,12,22,24-tetranitro derivative of I — see Table 1.

Note: In the foregoing and other examples, the decomposition temperatures are uncorrected and were made in capillary tubes in a Mel-Temp apparatus using a 500°C. thermometer. NMR spectra were determined in the stated solvent on a Varian T-60 spectrometer using tetramethylsilane as internal reference.

PERFORMANCE TESTS

The octanitro compound obtained in Example 1, Part B was tested by the "260 Vacuum Thermal Stability Test For Explosives" (reference: H. T. Simmons Naval Ordnance Laboratory Technical Report 70-142). It showed an evolution of 2.1 ml. gas/gm./hr., thereby qualifying the compound as "thermally stable".

The compound was also tested for sensitivity to explosion on impact by the Picatinny Arsenal Method, described briefly in AMC Pamphlet 706-177, "Engineering Design Handbook-Explosive Series-Properties of Explosives of Military Interest", January, 1971, pages 1–2 and more fully in references cited therein. The impact test value (the minimum height at which at least one of 10 trials results in explosion) was 3 inches, compared to the following impact test values for known explosives: TNT-14 inches; RDX and HMX-8 to 9 inches; PETN-5 to 6 inches; tetryl-5 to 6 inches.

EXAMPLE 2

Part A

The procedure described in Example 1, Part A was repeated using an equivalent amount of 5-methylresorcinol in place of resorcinol, except that the compound was isolated by pouring the reaction mixture into 10 volumes of hot water followed by refluxing for 1 hour to coagulate the product, which is otherwise difficult to filter. The compound melted at 320°C. and was obtained 90% of theory yield. The structure of the compound was established as the 11,23-dimethyl derivative of I by elemental analysis and NMR (Table 1).

Part B

The compound obtained in Part A was converted to an octanitro compound according to the procedure described under Example 1, Part B. The yield was 97% of theory. After recrystallization from aqueous DMF the compound flashed at 360°C. Based on elemental analysis, and NMR analysis, the compound is believed to be the 11,23-dimethyl-10,12,22,24-tetranitro derivative of I (see Table 1).

EXAMPLE 3

Part A

The procedure described in Example 1, Part A was repeated using an equivalent amount of 2-methylresorcinol. The compound was obtained in 62% of theory yield. Recrystallized from DMF, it decomposed at 400°C. Elemental analysis showed the compound to be the 25,27-dimethyl derivative of I (see Table 1).

Part B

The compound obtained in Part A was converted to an octanitro compound by heating it for 4 hours at 135°C. with a mixture of 15.2g of 98% nitric acid and 92g of 96% sulfuric acid. The yield was 64% of theory. After recrystallization from nitrobenzene it flashed at 348°C. Molecular weight and elemental analyses agreed with the theoretical for the dimethyltetranitro derivative of I (see Table 1).

EXAMPLE 4

Part A

The procedure described in Example 1, Part A was repeated, using an equivalent amount of 2-nitroresorcinol, except that after completion of the reaction the mixture was allowed to stand overnight for separation of the product. The mixture was filtered and the filter cake was boiled with water to remove sodium chloride. The yield of product was 83% of theory. After recrystallization from nitrobenzene it flashed at 385°C. The compound was shown to be the 25,27-dinitro derivative of I (Table 1).

Part B

The compound obtained in Part A was converted to an octanitro compound by nitration for 6 hours at 140°–160°C. following the procedure of Example 1. The yield of octanitro compound thus obtained was 70% of theory. After recrystallization from DMF the compound flashed at 355°C. Based on elemental analysis and mass spectrometric molecular weight, the product is believed to be a mixture of the 10,22(24),25,27-tetranitro derivatives of I, i.e. a mixture of isomers containing nitro groups in the 22- or 24-positions (see Table 1).

Table 1 shows the analytical and other data relating to the compounds produced in Examples 1–4.

In similar manner, by following the procedure described in Example 2, Part A and employing in place of 5-methylresorcinol an equivalent amount of 2-ethylresorcinol, 2-n-propylresorcinol, 5-n-propylresorcinol, 5-n-butylresorcinol, 5-n-amylresorcinol and 5-n-hexylresorcinol, the corresponding dialkyl derivatives of I, including isomeric mixtures, were obtained. These compounds were converted to the corresponding tetranitro derivatives of I according to the procedure described in Example I, Part B. The octanitro compounds thus obtained were explosives possessing good impact sensitivity and thermal stability.

EXAMPLE 5

Part A

The procedure described in Example 1, Part A was followed, using an equivalent amount of hydroquinone, except that after completion of the reaction the mixture was allowed to stand overnight for separation of the product. The mixture was filtered and the filter cake was boiled with water to remove sodium chloride. The yield of product was 44% of theory. After recrystallization from nitrobenzene the product decomposed at 433°C. The compound was identified as having the structure II by elemental analysis, NMR and mass spectrometric molecular weight.

Part B

The compound obtained in Part A was converted to an octanitro compound by nitration for 4 hours at 105°C. following the procedure of Example 1. The yield of octanitro compound was 35% of the theory. The crude product was purified by slurrying it with cold acetone to extract the tetranitro derivative of II from the insoluble II. The solution was diluted to turbidity with n-butanol and heated to boiling to precipitate the tetranitro derivative of II, which had a flash point of 348°C. It was shown to be a mixture of octanitro compounds by elemental analysis, mass spectrometric molecular weight and NMR. The product was an explosive possessing good thermal stability. The analytical and other data for the compounds of Example 5 are shown in Table 2.

EXAMPLE 6

Part A

Using the procedure of Example 5, Part A but employing 2-methylhydroquinone in place of hydroquinone, there was obtained the dimethyl derivative of II, probably as a mixture of the 10,21- and 10,22-dimethyl isomers. The product was obtained in 45% theory yield and decomposed at 392°C. Analysis: C, 54.2 (54.1 found); H,2.8 (2.9 found); N,9.7 (9.9 found).

Part B

The compound obtained in Part A was converted to a tetranitro derivative of II by the procedure described in Example 5, Part B.

In similar manner, by employing the procedure described in Example 5, Part A, but using in place of hydroquinone an equivalent amount of 2-ethylhydroquinone, 2-n-propylhydroquinone, 2-n-butylhydroquinone and 2-n-hexylhydroquinone, the corresponding dialkyl derivatives of II were obtained. These compounds were converted to the corresponding tetranitro derivatives of II according to the procedure described in Example 5, Part B. The octanitro compounds thus obtained were explosives possessing good thermal stability and impact sensitivity.

The foregoing disclosure is merely illustrative of the principles of this invention and is not to be interpreted in a limiting sense. I wish it to be understood that I do not desire to be limited to exact details of construction shown and described, because obvious modifications will occur to a person skilled in the art.

TABLE 1

| Example | Substituents on Resorcinol | Substituents on I | Mol. Wt. (Found) | Molecular Formula | Carbon (Found) | Hydrogen (Found) | Nitrogen (Found) | NMR Spectra |
|---|---|---|---|---|---|---|---|---|
| 1 Part A | none | none | 548 (548) | $C_{24}H_{12}N_4O_{12}$ | 52.6 (52.6) | 2.2 (2.4) | 10.2 (9.9) | (DMSO**-$d_6$),9.00(1H) 7.30(4H),6.73$_{ppm}$(1H) |
| 1 Part B | | 10,12,22,24-tetranitro | 728 (728) | $C_{24}H_8N_8O_{20}$ | 39.5 (39.2) | 1.1 (1.4) | 15.4 (14.9) | (Acetone-$d_6$),9.00(1H) 7.97(1H) |
| 2 Part A | 5-methyl | 11,23-dimethyl | | $C_{26}H_{16}N_4O_{12}$ | 54.1 (54.0) | 2.8 (2.9) | 9.7 (9.4) | (DMSO-$d_6$),8.93(1H),7.07 (3H),6.82(1H),2.37(3H) |
| 2 Part B | | 11,23-dimethyl-10,12,22,24-tetranitro* | | $C_{26}H_{12}N_8O_{20}$ | 41.4 (41.7) | 1.6 (1.7) | 14.8 (14.7) | Not determined |

TABLE 1-continued

| Example | Substituents on Resorcinol | Substituents on I | Mol. Wt. (Found) | Molecular Formula | Carbon (Found) | Hydrogen (Found) | Nitrogen (Found) | NMR Spectra |
|---|---|---|---|---|---|---|---|---|
| 3 Part A | 2-methyl | 25,27-dimethyl | | $C_{26}H_{16}N_4O_{12}$ | 54.1 (54.3) | 2.8 (3.1) | 9.7 (9.9) | Not determined |
| 3 Part B | | 25,27-dimethyl-10,12,22,24-tetranitro* | 756 (756) | $C_{26}H_{12}N_8O_{20}$ | 41.4 (41.3) | 1.6 (1.7) | 14.8 (13.8) | Not determined |
| 4 Part A | 2-nitro | 25,27-dinitro | 638 (638) | $C_{24}H_{10}N_6O_{16}$ | 45.2 (45.5) | 1.6 (1.7) | 13.2 (13.1) | Not determined |
| 4 Part B | | 10,22(24),25,27-tetranitro* | 728 (728) | $C_{24}H_8N_8H_{20}$ | 39.5 (39.7) | 1.1 (1.3) | 15.4 (14.7) | Not determined |

*The positions occupied by the entering nitro groups were not established but are assumed by analogy to the octanitro compound of Example 1, Part B.
**Dimethylsulfoxide Table 2

| Substituents on Hydroquinone | Substituents on II | Molecular Formula | Carbon (Found) | Hydrogen (Found) | Nitrogen (Found) | MNR |
|---|---|---|---|---|---|---|
| None | | $C_{24}H_{12}N_4O_{12}$ | 52.6 (52.5) | 2.2 (2.4) | 10.2 (10.5) | (DMSO-$d_6$),907(1H),7.83(1H),77.7(1H),2.43(3H) |
| | Tetranitro | $C_{24}H_8N_8O_{20}$ | 39.5 (39.8) | 1.1 (1.4) | 15.4 (14.6) | (Acetone-$d_6$),9.07(1H),7.08(1H),7.03–8.20(2H) |

I claim:
1. A nitro compound of the formula

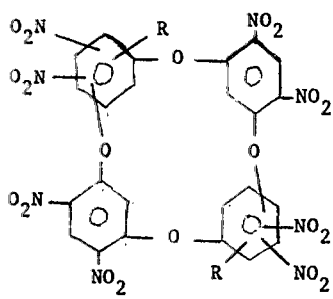

wherein R is hydrogen or lower n-alkyl and the ether oxygen atoms are attached in the 1,3 or 1,4 positions to the R substituted benzene rings, R being in the 2 or 5 positions when the ether oxygen atoms are in the 1,3 positions and R is lower n-alkyl.

2. The nitro compound of claim 1, wherein the ether oxygen atoms are attached in the 1,3 positions to the R-substituted benzene rings.

3. The nitro compound of claim 2, wherein R is hydrogen.

4. The nitro compound of claim 2, wherein R is lower n-alkyl.

5. The nitro compound of claim 4, wherein R is methyl.

6. The nitro compound of claim 1, wherein the ether oxygen atoms are attached in the 1,4 positions to the R-substituted benzene rings.

7. The nitro compound of claim 6, wherein R is hydrogen.

8. The nitro compound of claim 6, wherein R is lower n-alkyl.

9. The nitro compound of claim 8, wherein R is methyl.

10. The process of preparing a nitro compound of the formula

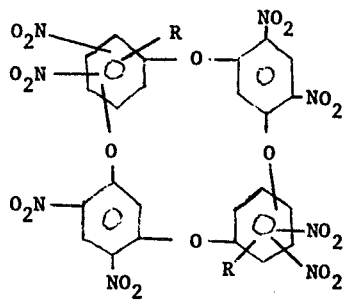

wherein R is hydrogen or lower n-alkyl and the ether oxygen atoms are attached in the 1,3 or 1,4 positions to the R substituted benzene rings, R being in the 2 or 5 positions when the ether oxygen atoms are in the 1,3 positions and R is lower n-alkyl, which comprises reacting a compound of the formula werein R is hydrogen, lower n-alkyl or nitro and the ether oxygen atoms are attached in the 1,3 or 1,4 positions to the R substituted benzene rings, R being in the 2 or 5 positions when the ether oxygen atoms are in the 1,3 positions and R is lower n-alkyl or nitro, with conc. nitric acid.

11. The process of claim 10, wherein the nitric acid is mixed with conc. sulfuric acid.

* * * * *